(12) United States Patent
Kain et al.

(10) Patent No.: US 7,835,871 B2
(45) Date of Patent: Nov. 16, 2010

(54) NUCLEIC ACID SEQUENCING SYSTEM AND METHOD

(75) Inventors: Robert C. Kain, San Diego, CA (US); David L. Heiner, San Diego, CA (US); Chanfeng Zhao, San Diego, CA (US); Kevin Gunderson, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 128 days.

(21) Appl. No.: 12/020,721

(22) Filed: Jan. 28, 2008

(65) Prior Publication Data

US 2008/0262747 A1 Oct. 23, 2008

Related U.S. Application Data

(60) Provisional application No. 60/897,647, filed on Jan. 26, 2007, provisional application No. 60/897,646, filed on Jan. 26, 2007.

(51) Int. Cl.
*G06F 19/00* (2006.01)
*C12Q 1/68* (2006.01)

(52) U.S. Cl. .............................. 702/20; 435/6
(58) Field of Classification Search ........................ None
See application file for complete search history.

(56) References Cited

U.S. PATENT DOCUMENTS

| | | | |
|---|---|---|---|
| 4,042,338 A | 8/1977 | Huber | |
| 5,202,418 A | 4/1993 | Lebl et al. | |
| 5,338,831 A | 8/1994 | Lebl et al. | |
| 5,342,585 A | 8/1994 | Lebl et al. | |
| 5,434,083 A | 7/1995 | Mitsumaki et al. | |
| 5,614,608 A | 3/1997 | Krchnak et al. | |
| 6,045,760 A | 4/2000 | Aizawa et al. | |
| 6,121,054 A | 9/2000 | Lebl | |
| 6,130,046 A | 10/2000 | Hubbell et al. | |
| 6,264,891 B1 | 7/2001 | Heyneker et al. | |
| 6,335,166 B1 | 1/2002 | Ammann et al. | |
| 6,663,832 B2 | 12/2003 | Lebl et al. | |
| 6,839,454 B1 | 1/2005 | Park | |
| 6,846,460 B1 | 1/2005 | Lebl | |
| 2002/0044894 A1 | 4/2002 | Lebl et al. | |
| 2003/0196695 A1 | 10/2003 | O'Connor et al. | |
| 2004/0219063 A1 | 11/2004 | Heiner et al. | |
| 2006/0083428 A1 | 4/2006 | Ghosh et al. | |
| 2006/0293558 A1 | 12/2006 | De Groen et al. | |
| 2007/0114362 A1 | 5/2007 | Feng et al. | |
| 2007/0117178 A1 | 5/2007 | Heiner et al. | |

FOREIGN PATENT DOCUMENTS

| | | |
|---|---|---|
| EP | 0445915 A1 | 1/1991 |
| WO | 99/08233 A | 2/1999 |
| WO | 00/44491 A2 | 8/2000 |
| WO | 02/04123 A1 | 1/2002 |
| WO | 02/16040 A1 | 2/2002 |
| WO | WO 2006/064199 * | 6/2006 |
| WO | 2006113931 A | 10/2006 |
| WO | 2007/123744 A2 | 11/2007 |

OTHER PUBLICATIONS

Margulies et al. Genome sequencing in microfabricated high-density picolitre reactors Nature vol. 437, pp. 376-380 (2005).*
Jianping Hua et al., "Microarray BASICA: background adjustment, segmentation, image compression and analysis of microarray images," EURASIP Journal on Applied Signal Processing, vol. 2004, No. 1; Jan. 1, 2004; pp. 92-107.
Luo et al., "Storage and Transmission of Microarray images," Drug Discovery Today, vol. 10, No. 23-24; Dec. 1, 2005, pp. 1689-1695.
Adjeroh et al., "On denoising and compression of DNA microarray images," Pattern Recognition, vol. 39, No. 12, Dec. 1, 2006, pp. 2478-2493.
Klincewicz,; "Hub Location in backbone/tributary network design: a review"; Location Science, vol. 6, pp. 307-335 (1998).
Rahnenfuhrer et al.; "Hybrid clustering for microarray image analysis combining intensity and shape features"; BMC Bioinformatics, vol. 5, Article 47 (2004).
Shendure et al.; "Accurate Multiplex Polony Sequencing of an Evolved Bacterial Genome," Science, vol. 309, pp. 1728-1732, and supplemental material (2005).

* cited by examiner

*Primary Examiner*—John S Brusca
(74) *Attorney, Agent, or Firm*—Fletcher Yoder PC

(57) ABSTRACT

A technique for sequencing nucleic acids in an automated or semi-automated manner is disclosed. Sample arrays of a multitude of nucleic acid sites are processed in multiple cycles to add nucleotides to the material to be sequenced, detect the nucleotides added to sites, and to de-block the added nucleotides of blocking agents and tags used to identify the last added nucleotide. Multiple parameters of the system are monitored to enable diagnosis and correction of problems as they occur during sequencing of the samples. Quality control routines are run during sequencing to determine quality of samples, and quality of the data collected.

34 Claims, 8 Drawing Sheets

NUCLEIC ACID SEQUENCING SYSTEM AND METHOD

CROSS REFERENCE TO RELATED APPLICATIONS

This application claims priority of U.S. Provisional Patent Application No. 60/897,646, entitled "Image Data Efficient Genetic Sequencing Method and System," filed Jan. 26, 2007, which is herein incorporated in its entirety by reference, and of U.S. Provisional Patent Application No. 60/897,647, entitled "Nucleic Acid Sequencing System and Method," filed Jan. 26, 2007, which is herein incorporated in its entirety by reference.

BACKGROUND

The present invention relates generally to the field of genetic sequencing. More particularly, the invention relates to improved techniques for permitting automated sequencing of genetic materials by use of arrays of genetic fragments.

Genetic sequencing has become an increasingly important area of genetic research, promising future uses in diagnostic and other applications. In general, genetic sequencing consists of determining the order of nucleotides for a nucleic acid such as a fragment of RNA or DNA. Relatively short sequences are typically analyzed, and the resulting sequence information may be used in various bioinformatics methods to align fragments against a reference sequence or to logically fit fragments together so as to reliably determine the sequence of much more extensive lengths of genetic material from which the fragments were derived. Automated, computer-based examination of characteristic fragments have been developed, and have been used more recently in genome mapping, analysis of genetic variation between individuals, identification of genes and their function, and so forth. However, existing techniques are highly time-intensive, and resulting genomic information is accordingly extremely costly.

A number of alternative sequencing techniques are presently under investigation and development. These include the use of microarrays of genetic material that can be manipulated so as to permit parallel detection of the ordering of nucleotides in a multitude of fragments of genetic material. The arrays typically include many sites formed or disposed on a substrate. Additional materials, typically single nucleotides or strands of nucleotides (oligonucleotides) are introduced and permitted or encouraged to bind to the template of genetic material to be sequenced, thereby selectively marking the template in a sequence dependent manner. Sequence information may then be gathered by imaging the sites. In certain current techniques, for example, each nucleotide type is tagged with a fluorescent tag or dye that permits analysis of the nucleotide attached at a particular site to be determined by analysis of image data.

Although such techniques show promise for significantly improving throughput and reducing the cost of sequencing, further progress in the speed and reliability of the analytical steps involved in sequencing is desirable.

BRIEF DESCRIPTION

The present invention provides significant improvements in the field of nucleic acid sequencing, especially with regard to instrumentation and analysis methods. The techniques may be used for any desired sequencing, and will typically be most useful in sequencing of DNA and RNA (including cDNA). The techniques are based upon analysis of nucleotide sequences in samples supported on a substrate, and typically containing a multitude of individual sites such as in a nucleic acid array. Moreover, the techniques may be used with a variety of sequencing approaches or technologies, including techniques often referred to as sequencing-by-synthesis (SBS), sequencing-by-ligation, pyrosequencing and so forth. The present techniques have been found or are believed to provide for more highly automated or higher quality sequencing, permitting higher throughput and ultimately reduced sequence costs.

Accordingly, the invention provides a method for sequencing a plurality of nucleic acids which can include the steps of (a) beginning a cycle of a sequencing procedure for an array having a plurality of nucleic acids via a system capable of determining nucleotide sequence of the array; (b) evaluating a parameter of the system; (c) altering the sequencing procedure for the array based on the parameter; and (d) performing another cycle of the sequencing procedure for the array.

The invention further provides a method for sequencing a plurality of nucleic acids which includes the steps of (a) performing an automated nucleic acid sequencing operation; (b) generating data based upon the operation; and (c) evaluating a quality of the sample based upon the data.

Also provided is a method for sequencing a plurality of nucleic acids, including the steps of (a) performing a cycle of a sequencing procedure for an array having a plurality of nucleic acids via a system capable of determining nucleotide sequence of the array; (b) detecting a plurality of signals indicative of nucleotides present at sites of the array; (c) evaluating the signals to determine quality of the array; and (d) altering the sequencing procedure for the array based on the quality.

A method for sequencing a plurality of nucleic acids can include steps of (a) introducing a process fluid to an array or nucleic acids in a system performing a nucleic acid sequencing procedure for the array; and (b) performing via the system at least one cycle of the sequencing procedure for the array; wherein the process fluid is heated or cooled prior to introduction to the array.

A method for sequencing a plurality of nucleic acids can include the steps of (a) performing a cycle of a sequencing procedure for an array comprising a plurality of nucleic acids via a system capable of determining nucleotide sequence of the array; (b) detecting a plurality of signals indicative of nucleotides present at sites of the array; and (c) repeating steps (a) and (b); wherein scheduling of steps (a) and (b) is temporally decoupled.

A method for sequencing a plurality of nucleic acids can include the steps of (a) performing a cycle of a sequencing procedure for an array having a plurality of nucleic acids via a system capable of determining nucleotide sequence of the array; (b) imaging the array to generate image data; (c) deriving sequence data from the image data, the sequence data indicative of nucleotide species present at a position in the sequence of a nucleic acid of the array; (d) repeating steps (a), (b) and (c); and (e) retaining the sequence data and deleting at least a portion of the image data from which the sequence data was derived prior to completion of the sequencing procedure on the array.

The invention also provides a system for sequencing a plurality of nucleic acids. The system can include a plurality of processing stations configured to add tagged nucleotides to sites of an array; and a plurality of detecting stations interspersed with the processing stations for detecting nucleic acid sequences of the sites and generating data representative thereof.

Also provided is a system for sequencing a plurality of nucleic acids including a fluidics handling system for facilitating assay reaction protocols; an imaging system for acquiring sequencing data; diagnostic components configured to measure system parameters during operation of the sequencing system; quality evaluation circuitry configured to assess a quality of the sequencing system based upon a multiple step analysis; and control circuitry configured to alter operating conditions of the sequencing system based upon data collected by the diagnostic components or the quality evaluation circuitry.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
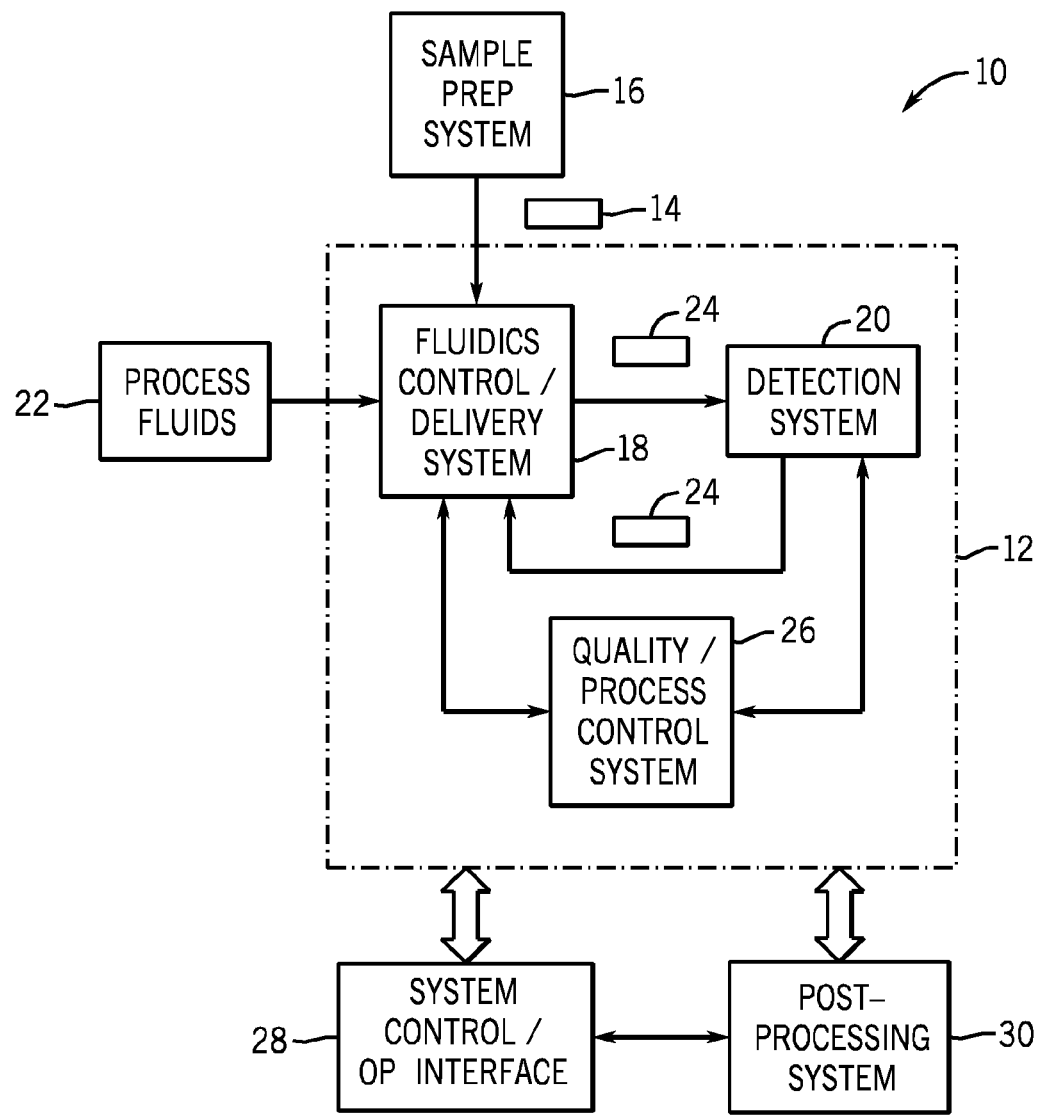
FIG. 1 is a diagrammatical overview of a sequencing system incorporating aspects of the present technique.

Turning now to the drawings, referring first to FIG. 1, a diagrammatical representation of a sequencing system 10 is illustrated as including a sequencer 12 designed to determine sequences of genetic material of a sample 14. The sequencer may function in a variety of manners, and based upon a variety of techniques, including sequencing by primer extension using labeled nucleotides, as in a presently contemplated embodiment, as well as other sequencing techniques such as sequencing by ligation or pyrosequencing. In general, and as described in greater detail below, the sequencer 12 progressively moves samples through reaction cycles and imaging cycles to progressively build oligonucleotides by binding nucleotides to templates at individual sites on the sample. In a typical arrangement, the sample will be prepared by a sample preparation system 16. This process may include amplification of fragments of DNA or RNA on a support to create a multitude of sites of DNA or RNA fragments the sequence of which are determined by the sequencing process. Exemplary methods for producing sites of amplified nucleic acids suitable for sequencing include, but are not limited to, rolling circle amplification (RCA) (Lizardi et al., *Nat. Genet.* 19:225-232 (1998)), bridge PCR (Adams and Kron, *Method for Performing Amplification of Nucleic Acid with Two Primers Bound to a Single Solid Support*, Mosaic Technologies, Inc. (Winter Hill, Mass.); Whitehead Institute for Biomedical Research, Cambridge, Mass., (1997); Adessi et al., *Nucl. Acids Res.* 28:E87 (2000); Pemov et al., *Nucl. Acids Res.* 33:e11(2005); or U.S. Pat. No. 5,641,658), polony generation (Mitra et al., *Proc. Natl. Acad. Sci. USA* 100:5926-5931 (2003); Mitra et al., *Anal. Biochem.* 320:55-65 (2003)), or clonal amplification on beads using emulsions (Dressman et al., *Proc. Natl. Acad. Sci. USA* 100:8817-8822 (2003)) or ligation to bead-based adapter libraries (Brenner et al., *Nat. Biotechnol.* 18:630-634 (2000); Brenner et al., *Proc. Natl. Acad. Sci. USA* 97:1665-1670 (2000)); Reinartz, et al., *Brief Funct. Genomic Proteomic* 1:95-104 (2002)). The sample preparation system 16 will typically dispose the sample, which may be in the form of an array of sites, in a sample container for processing and imaging.

The sequencer 12 includes a fluidics control/delivery system 18 and a detection system 20. The fluidics control/delivery system 18 will receive a plurality of process fluids as indicated generally by reference numeral 22, for circulation through the sample containers of the samples in process, designated generally by reference numeral 24. As will be appreciated by those skilled in the art, the process fluids will vary depending upon the particular stage of sequencing. For example, in SBS using labeled nucleotides, the process fluids introduced to the sample will include a polymerase and tagged nucleotides of the four common DNA types, each nucleotide having a unique fluorescent tag and a blocking agent linked to it. The fluorescent tag allows the detection system 20 to detect which nucleotides were last added to probes hybridized to template nucleic acids at individual sites in the array, and the blocking agent prevents addition of more than one nucleotide per cycle at each site. In other processes, such as sequencing by ligation, the process fluids at this stage will include query probes with unique fluorescent tags attached thereto. Similarly, the query probes will bind to the templates at each site in a configuration that allows ligation of the query probes to an anchor primer and may be detected by the detection system 20 for sequencing of the templates at each site.

At other phases of the sequencing cycles, the process fluids 22 will include other fluids and reagents such as reagents for removing extension blocks from nucleotides, cleaving nucleotide linkers, or for removing bases from ligated oligonucleotides to release a newly extendable probe terminus. For example, once reactions have taken place at individual sites in the array of the samples, the initial process fluid containing the tagged nucleotides will be washed from the sample in one or more flushing operations. The sample may then undergo detection, such as by the optical imaging at the detection system 20. Subsequently, reagents will be added by the fluidics control/delivery system 18 to de-block the last added nucleotide and remove the fluorescent tag from each. The fluidics control/delivery system 18 will typically then again wash the sample, which is then prepared for a subsequent cycle of sequencing. Exemplary fluidic and detection configurations that can be used in the methods and devices set forth herein are described in WO 07/123,744. In general, such sequencing may continue until the quality of data derived from sequencing degrades due to cumulative loss of yield or until a predetermined number of cycles have been completed, as described in greater detail below.

The quality of samples 24 in process as well as the quality of the data derived by the system, and the various parameters used for processing the samples is controlled by a quality/process control system 26. The quality/process control system 26 will typically include one or more programmed processors, or general purpose or application-specific computers which communicate with sensors and other processing systems within the fluidics control/delivery system 18 and the detection system 20. A number of process parameters, discussed in further detail below, may be used for sophisticated quality and process control, for example, as part of a feedback loop that can change instrument operation parameters during the course of a sequencing run.

The sequencer 12 also communicates with a system control/operator interface 28 and ultimately with a post-processing system 30. Here again, the system control/operator interface 28 will typically include a general purpose or application-specific computer designed to monitor process parameters, acquired data, system settings, and so forth. The operator interface may be generated by a program executed locally or by programs executed within the sequencer 12. In general, these may provide visual indications of the health of the systems or subsystems of the sequencer, the quality of the data acquired, and so forth. The system control/operator interface 28 may also permit human operators to interface with the system to regulate operation, initiate and interrupt sequencing, and any other interactions that may be desired with the system hardware or software. For instance, the system control/operator interface 28 may automatically undertake and/or modify steps to be performed in a sequencing procedure, without input from a human operator. Alternatively or additionally, the system control/operator interface 28 may generate recommendations regarding steps to be performed in a sequencing procedure and display these recommendations to the human operator. This mode would, of course, allow for input from the human operator before undertaking and/or modifying steps in the sequencing procedure. In addition, the system control/operator interface 28 may provide an option to the human operator allowing the human operator to select certain steps in a sequencing procedure to be automatically performed by the sequencer 12 while requiring input from the human operator before undertaking and/or modifying other steps. In any event, allowing both automated and operator interactive modes may provide increased flexibility in performing the sequencing procedure. In addition, the combination of automation and human-controlled interaction may further allow for a system capable of creating and modifying new sequencing procedures and algorithms through adaptive machine learning based on the inputs gathered from human operators.

The post-processing system 30 will typically also include one or more programmed computers that receive detected information, which may be in the form of pixilated image data and derive sequence data from the image data. The post-processing system 30 may include image recognition algorithms which distinguish between colors of dyes attached to nucleotides that bind at individual sites as sequencing progresses (e.g., by analysis of the image data encoding specific colors or intensities), and logs the sequence of the nucleotides at the individual site locations. Progressively, then, the post-processing system 30 will build sequence lists for the individual sites of the sample array which can be further processed to establish genetic information for extended lengths of material by various bioinformatics algorithms.

Figure 2:
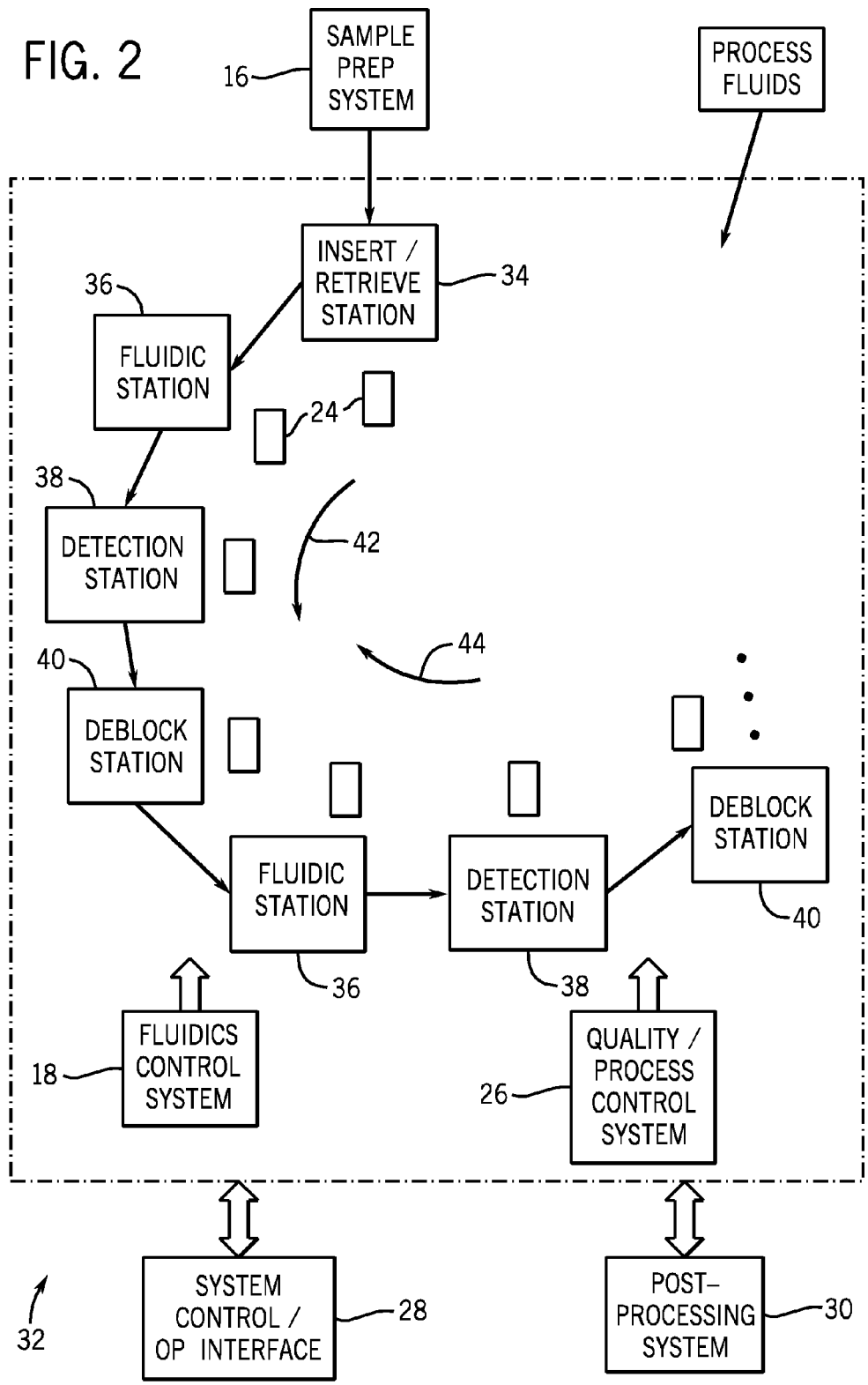
FIG. 2 is a diagrammatical overview of a multi-station sequencing system implementing aspects of the present technique.

The sequencing system 10 may be configured to handle individual samples or may be designed for higher throughput in a manner generally represented in FIG. 2. FIG. 2 illustrates a multi-station sequencer 32 in which multiple stations are provided for the delivery of reagents and other fluids, and for detection of progressively building sequences of nucleotides. In the illustrated embodiment, the sequencer 32 may include a series of stations disposed in a plane, such as on a table, or in multiple planes. To allow samples to be inserted into the sequencer, an insertion/retrieval station 34 will typically be provided. This station will be physically configured to allow a human operator or robot to insert a sample into the device and lodge the sample in a process flow for sequencing operations to be automatically performed at the various additional stations. From the insertion/retrieval station 34, a mechanical conveying system (not illustrated) will serve to move the samples 24 and process between the other stations.

In the embodiment illustrated in FIG. 2, the additional stations will include fluidic stations 36, detection stations 38, and de-blocking stations 40, although other stations may be included or interspersed with these stations depending upon the process and sequence of steps desired. For example, fluidic stations 36 will serve to introduce reagents and other process fluids to the samples 24, such as to allow for binding of individual nucleotides as sequencing progresses. The fluidic stations 36 may also allow for washing or flushing reagents from the samples. Alternatively or additionally, the stage supporting the sample can be configured to allow removal of liquids, including reagents present in the liquids, from samples independent of their location in the system. For example, the stage can include valve actuated vacuum lines that can be activated for removal of liquids from the sample when the sample is at any station or even when the sample is between stations. A useful vacuum system is described, for example, in pending U.S. patent application Ser. No. 11/521,574, which is incorporated herein by reference.

The detection stations 38 may include any desired detection circuitry, such as optical, electrical, or other equipment designed to detect the particular nucleotides added at individual sites of the sample as the sequencing progresses. An exemplary optical system for such detection is described below with reference to FIG. 3. The de-blocking station 40 may be employed for delivering reagents used to remove protective molecules that prevent binding of more than one nucleotide at a time, particularly in SBS systems. The de-blocking station 40 may also be used to cleave fluorescent dyes and similar molecules from the nucleotides or oligonucleotides as sequencing progresses.

In general, the samples 24 may progress through the sequencer 32 in a progressive flow direction as indicated generally by arrow 42. This may correspond to a normal flow of the sample through the sequencer. However, the samples may retrogress in the stations as indicated generally by reference numeral 44. Such retrogression may be desired to permit re-imaging of the samples, reintroduction of reagents, re-flushing, or generally any repetitive operation that can be performed by a preceding station. It should also be noted that the progression of samples in the system, as also in the system of FIG. 1, may be decoupled in a temporal sense. That is, not all samples need to progress through the stations for the same number of cycles nor do all samples need to enter and exit a multi-cycle process in the same cycle.

Samples may be removed from processing, reprocessed, and scheduling of such processing may be altered in real time, particularly where the fluidics control system 18 or the quality/process control system 26 detect that one or more operations were not performed in an optimal or desired manner. In embodiments wherein a sample is removed from the process or experiences a pause in processing that is of a substantial duration, the sample can be placed in a storage state. Placing the sample in a storage state can include altering the environment of the sample or the composition of the sample to stabilize biomolecule reagents, biopolymers or other components of the sample. Exemplary methods for altering the sample environment include, but are not limited to, reducing temperature to stabilize sample constituents, addition of an inert gas to reduce oxidation of sample constituents, and removing from a light source to reduce photobleaching or photodegradation of sample constituents. Exemplary methods of altering sample composition include, without limitation, adding stabilizing solvents such as antioxidants, glycerol and the like, altering pH to a level that stabilizes enzymes, or removing constituents that degrade or alter other constituents. In addition, certain steps in the sequencing procedure may be performed before removing the sample from processing. For instance, if it is determined that the sample should be removed from processing, the sample may be directed to the fluidics control/delivery system 18 so that the sample may be washed before storage. Again, these steps may be taken to ensure that no information from the sample is lost.

Moreover, sequencing operations may be interrupted by the sequencer 12 at any time upon the occurrence of certain predetermined events. These events may include, without limitation, unacceptable environmental factors such as undesirable temperature, humidity, vibrations or stray light; inadequate reagent delivery or hybridization; unacceptable changes in sample temperature; unacceptable sample site number/quality/distribution; decayed signal-to-noise ratio; insufficient image data; and so forth. It should be noted that the occurrence of such events need not require interruption of sequencing operations. Rather, such events may be factors weighed by the quality/process control system 26 in determining whether sequencing operations should continue. For example, if an image of a particular cycle is analyzed in real time and shows a low signal for that channel, the image can be re-exposed using a longer exposure time, or have a particular chemical treatment repeated. If the image shows a bubble in a flow cell, the instrument can automatically flush more reagent to remove the bubble, then re-record the image. If the image shows zero signal for a particular channel in one cycle due to a fluidics problem, the instrument can automatically halt scanning and reagent delivery for that particular channel, thus saving on analysis time and reagent consumption.

Although the system has been exemplified above with regard to a system in which a sample interfaces with different stations by physical movement of the sample, it will be understood that the principles set forth herein are also applicable to a system in which the steps occurring at each station are achieved by other means not requiring movement of the sample. For example, reagents present at the stations can be delivered to a sample by means of a fluidic system connected to reservoirs containing the various reagents. Similarly, an optics system can be configured to detect a sample that is in fluid communication with one or more reagent stations. Thus, detection steps can be carried out before, during or after delivery of any particular reagent described herein. Accordingly, samples can be effectively removed from processing by discontinuing one or more processing steps, be it fluid delivery or optical detection, without necessarily physically removing the sample from its location in the device.

As in the system of FIG. 1, the various stations are coupled to the fluidics control system 18 and to the quality/process control system 26 to permit control of these operations, as well as control of quality of both the samples and of the operations performed at the various processing stations. Moreover, as in the system of FIG. 1, the various stations of the sequencer are linked to a system control/operator interface 28, and data collected is ultimately forwarded to a post-processing system 30 where sequence data is derived from the detected data, typically image data generated by the detection stations 38.

A system of the invention can be used to continuously sequence nucleic acids in a plurality of different samples. Systems of the invention can be configured to include an arrangement of samples and an arrangement of stations for carrying out sequencing steps. The samples in the arrangement of samples can be placed in a fixed order and at fixed intervals relative to each other. For example, an arrangement of nucleic acid arrays can be placed along the outer edge of a circular table. Similarly, the stations can be placed in a fixed order and at fixed intervals relative to each other. For example, the stations can be placed in a circular arrangement having a perimeter that corresponds to the layout for the arrangement of sample arrays. Each of the stations can be configured to carry out a different manipulation in a sequencing protocol. The two arrangements (i.e. sample arrays and stations) can be moved relative to each other such that the stations carry out desired steps of a reaction scheme at each reaction site. The relative locations of the stations and the schedule for the relative movement can correlate with the order and duration of reaction steps in the sequencing reaction scheme such that once a sample array has completed a cycle of interacting with the full set of stations, then a single sequencing reaction cycle is complete. For example, primers that are hybridized to nucleic acid targets on an array can each be extended by addition of a single nucleotide, detected and de-blocked if the order of the stations, spacing between the stations, and rate of passage for the array corresponds to the order of reagent delivery and reaction time for a complete sequencing reaction cycle.

In accordance with the configuration set forth above, and described in further detail below, each lap (or full revolution in embodiments where a circular table is used) completed by an individual sample array can correspond to determination of a single nucleotide for each of the target nucleic acids on the array (i.e. including the steps of incorporation, imaging, cleavage and de-blocking carried out in each cycle of a sequencing run). Furthermore, several sample arrays present in the system (for example, on the circular table) concurrently move along similar, repeated laps through the system, thereby resulting in continuous sequencing by the system. Using a system or method of the invention, reagents can be actively delivered or removed from a first sample array in accordance with a first reaction step of a sequencing cycle while incubation, or some other reaction step in the cycle, occurs for a second sample array. Thus, a set of stations can be configured in a spatial and temporal relationship with an arrangement of sample arrays such that reactions occur at multiple sample arrays concurrently even as the sample arrays are subjected to different steps of the sequencing cycle at any given time, thereby allowing continuous and simultaneous sequencing to be performed. The advantages of such a circular system are apparent when the chemistry and imaging times are disproportionate. For small flow cells that only take a short time to scan, it is advantageous to have a number of flow cells running in parallel in order to optimize the time the instrument spends acquiring data. When the imaging time and chemistry time are equal, a system that is sequencing a sample on a single flow cell spends half the time performing a chemistry cycle rather than an imaging cycle, and therefore a system that can process two flow cells could have one on the chemistry cycle and one on the imaging cycle. When the imaging time is ten fold less than the chemistry time, the system can have ten flow cells at various stages of the chemistry process whilst continually acquiring data.

Embodiments of the invention provide a system that is configured to allow replacement of a first sample array with a second sample array while the system continuously sequences nucleic acids of a third sample array. Thus, a first sample array can be individually added or removed from the system without interrupting sequencing reactions occurring at another sample array, thereby providing the advantage of continuous sequencing for the set of sample arrays. A further advantage is that sequencing runs of different lengths can be performed continuously and simultaneously in the system because individual sample arrays can complete a different number of laps through the system and the sample arrays can be removed or added to the system in an independent fashion such that reactions occurring at other sites are not perturbed.

Figure 3:
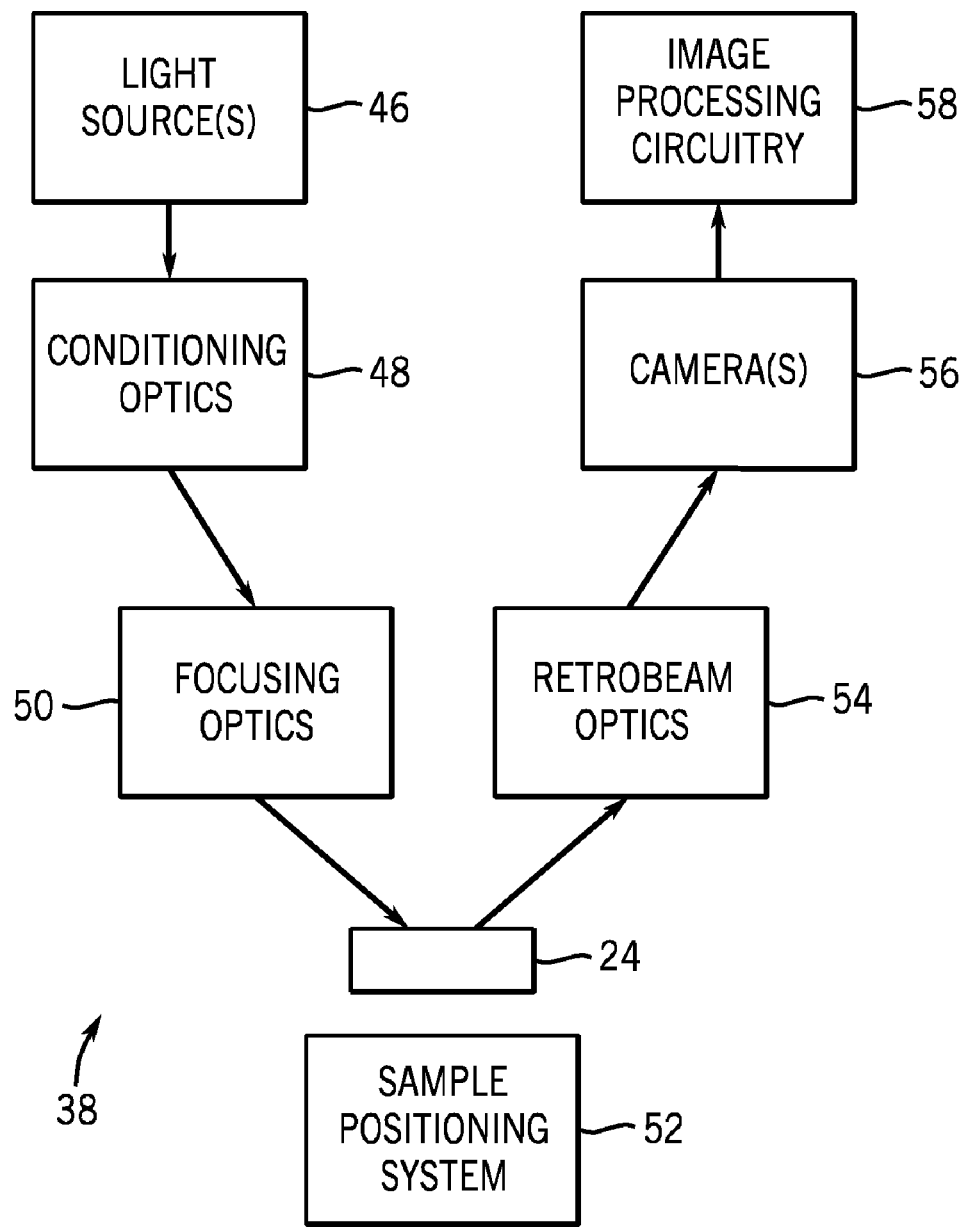
FIG. 3 is a diagrammatical overview of an exemplary imaging system that may be used in conjunction with the system of FIG. 1 or 2 for detection of sequences at individual sites in an array.

FIG. 3 illustrates an exemplary detection station 38 designed to detect nucleotides added at sites of an array in accordance with a presently contemplated optical system. As set forth above, a sample can be moved to two or more stations of the device that are located in physically different locations or alternatively one or more steps can be carried out on a sample that is in communication with the one or more stations without necessarily being moved to different locations. Accordingly, the description herein with regard to particular stations is understood to relate to stations in a variety of configurations whether or not the sample moves between stations, the stations move to the sample, or the stations and sample are static with respect to each other. In the embodiment illustrated in FIG. 3, one or more light sources 46 provide light beams that are directed to conditioning optics 48. The light sources 46 may include one or more lasers, with multiple lasers typically being used for detecting dyes that fluoresce at different corresponding wavelengths. The light sources may direct beams to the conditioning optics 48 for filtering and shaping of the beams in the conditioning optics. For example, in a presently contemplated embodiment, the conditioning optics 48 combine beams from multiple lasers and generate a generally linear beam of radiation that is conveyed to focusing optics 50. The laser modules can additionally include a measuring component that records the power of each laser. The measurement of power may be used as a feedback mechanism to control the length of time an image is recorded in order to obtain a uniform exposure energy, and therefore signal, for each image. If the measuring component detects a failure of the laser module, then the instrument can flush the sample with a "holding buffer" to preserve the sample until the error in the laser can be corrected.

The sample 24 is positioned on a sample positioning system 52 that may appropriately position the sample in three dimensions, and may displace the sample for progressive imaging of sites on the sample array. In a presently contemplated embodiment, the focusing optics 50 confocally direct radiation to one or more surfaces of the array at which individual sites are located that are to be sequenced. Depending upon the wavelengths of light in the focused beam, a retrobeam of radiation is returned from the sample due to fluorescence of dyes bound to the nucleotides at each site.

The retrobeam is then returned through retrobeam optics 54 which may filter the beam, such as to separate different wavelengths in the beam, and direct these separated beams to one or more cameras 56. The cameras 56 may be based upon any suitable technology, such as including charge coupled devices that generate pixilated image data based upon photons impacting locations in the devices. The cameras generate image data that is then forwarded to image processing circuitry 58. In general, the processing circuitry 58 may perform various operations, such as analog-to-digital conversion, scaling, filtering, and association of the data in multiple frames to appropriately and accurately image multiple sites at specific locations on the sample. The image processing circuitry 58 may store the image data, and will ultimately forward the image data to the post-processing system 30 where sequence data can be derived from the image data. Particularly useful detection devices that can be used at a detection station include, for example, those described in US 2007/0114362 (U.S. patent application Ser. No. 11/286,309) and WO 07/123,744, each of which is incorporated herein by reference.

Figure 4:
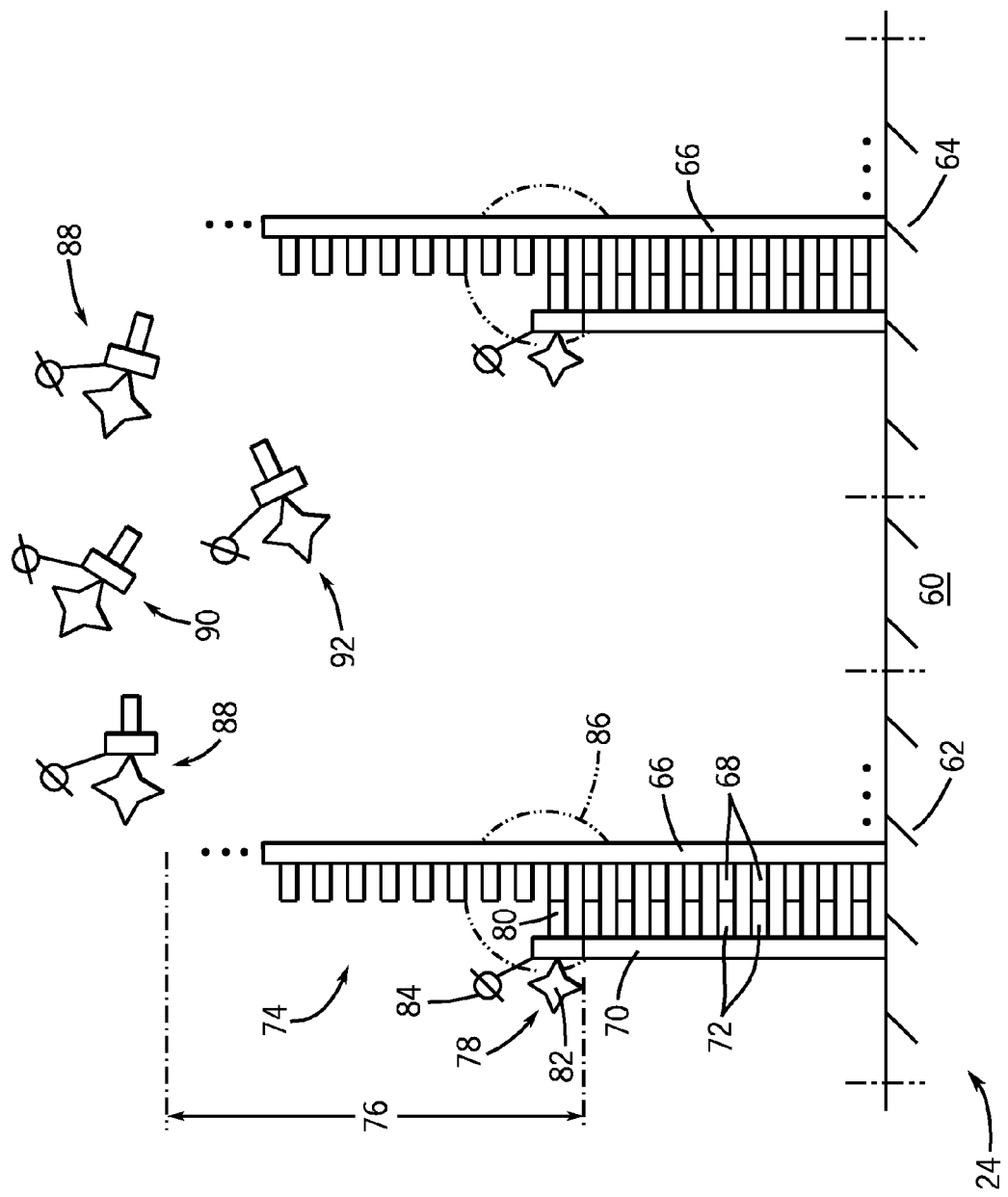
FIG. 4 is a diagrammatical representation of sequencing in the systems of the preceding figures in accordance with an SBS technique, as one example of the sequencing approach that may be used in the systems.

FIG. 4 illustrates a typical reaction cycle in a sequencing by synthesis technique for oligonucleotides that may benefit from the nucleotide recapture and recycling technique of the present invention. In general, the synthesis operation summarized in FIG. 4 may be performed on a sample 24 comprising a support 60 on which a multitude of sites 62 and 64 are formed. In the preparation of each sample 24, many such sites may be formed, each with unique fragments of genetic material as indicated generally by reference numeral 66. These fragments may constitute templates of DNA or RNA to be sequenced. The fragments can be isolated from a biological source using methods known in the art. In embodiments utilizing amplification methods, the fragments can be amplicons of a DNA or RNA isolated from a biological source. Each template comprises a number of mers or bases 68 which will uniquely bind to a complimentary nucleotide (or analog thereof) during the synthesis process. The sequencing process begins with binding of an anchor primer 70 to each of the templates. This anchor primer includes complementary bases 72 that bind with those of a portion of a template sequence. The remaining portion of the template, designated generally by reference numeral 74, constitutes that portion to be sequenced. The length 76 of the portion to be sequenced may vary, with presently contemplated embodiments extending from 25 to 40 bases or even as many as 50, 75, or 100 bases.

As sequencing progresses, the introduced processed stream will include all four common DNA nucleotides, one of which will add to the primer at a position that is opposite the next available base in the template, as indicated by reference numeral 78. The added nucleotide will include a base 80 that is complementary to the template as well as a fluorescent tag 82 and a blocking molecule 84. As will be noted by those skilled in the art, as used herein, the term "nucleotides" in the illustrated processes will typically include units from which DNA molecules are constructed. Although any nucleotides or oligonucleotides may be recaptured and recycled in accordance with the present technique, in many practical applications these will include deoxynucleotide-triphosphates (dNTP), each carrying a single nitrogenous base (adenine, guanine, cytosine or thymine). The complementary nucleotide is added to the primer due to the activity of a polymerase, as indicated generally by reference numeral 86. Other nucleotides than the specific one binding to the template will also be present in the process fluid, as indicated generally by reference numerals 88, 90, and 92 in FIG. 4. Nucleotides not binding to the templates will subsequently be washed from the sample in a flushing operation, exiting in the effluent stream to be recaptured and recycled as described above.

The sequencing system utilized of the type described above for analysis of oligonucleotide sequences may be automated and regulated in a number of ways. The present technique provides for automatic detection of a number of parameters of such systems and control of the sequencing process based upon such parameters. In general, the performance and quality control implemented by the present invention may allow for normal sequencing operations on one or many sample arrays, which may be altered based upon detected issues with performance or quality of the sample array, performance of the fluidics control/delivery system, performance of the detection system, or any subcomponent or subsystem of these. When exceptions or anomalies in quality or performance are detected, as described in greater detail below, remedial measures may be taken to correct the system performance, re-sequence or re-run certain sequencing cycle steps, such as nucleotide addition, imaging, de-blocking and so forth, or even interrupt sequencing altogether. Because the sequencing will represent an investment in terms of time and materials, the remedial measures may be adapted to continue sequencing if at all possible, while taking steps to guard against pursuing a synthesis procedure that is destined to fail or at least destined to produce results that are not of sufficient value to warrant the time and materials spent. Thus, the remedial measures improve the likelihood that reliable sequencing data will be obtained.

Figure 5:
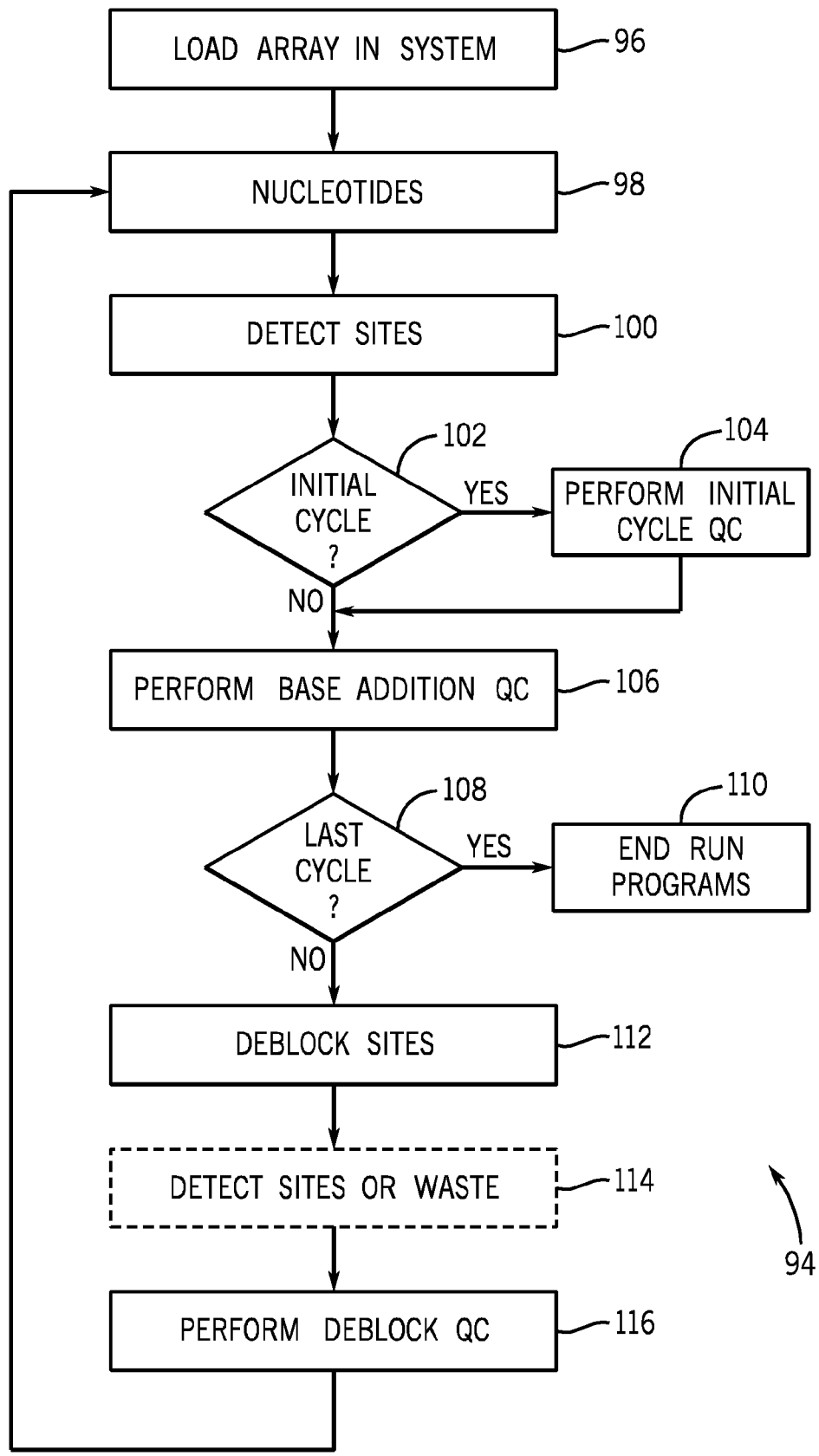
FIG. 5 is a flow chart illustrating exemplary logic for control of the sequencing and sample quality in accordance with aspects of the present technique.

FIG. 5 represents exemplary logic for carrying out and controlling a sequencing operation in accordance with this approach. The sequencing operation, denoted generally by reference numeral 94, begins with loading a sample array in the sequencing system, as indicated at step 96. As noted above, a number of different approaches may be employed, as may various configurations of arrays. In a presently contemplated embodiment, for example, arrays of a multitude of genetically different sites are employed, with each site being populated by a multitude of the same oligonucleotide, template, or fragment to be sequenced. The array may be loaded in a sample container and coupled to the fluidics control/delivery system such that reagents and other process fluids can be introduced to the sample and routed through the sample container for reactions (e.g., base addition and de-blocking), flushing, and so forth.

An array used in the invention can be any population of different reaction sites that are present at one or more substrates such that different reaction sites can be differentiated from each other according to their relative location. Typically, a single species of biopolymer, such as a nucleic acid, is attached at each individual reaction site. However, multiple copies of a particular species of biopolymer can be attached at a particular reaction site. The array taken as a whole will typically include a plurality of different biopolymers attached at a plurality of different sites. The reaction sites can be located at different addressable locations on the same substrate. Alternatively, an array can include separate substrates, such as beads, each bearing a different reaction sites.

At step 98 in FIG. 5, then, bases or nucleotides (or oligonucleotides in the case of processes such as sequencing-by-ligation or sequencing-by-hybridization) are added to the sites in the array in accordance with the particular sequencing approach adopted. Other biomolecule reagents used at this step can also be delivered including, for example, enzymes such as polymerase or ligase. For example, in SBS, polymerase and the four common nucleotide types, each including blocking agents and unique fluorescent dyes are introduced to the sample array and are allowed to react with the oligonucleotide templates at each site. Step 98 would also include, then, flushing the samples of the polymerase and nucleotides once sufficient time has elapsed for the desired reactions. At step 100, the sites and the most recently attached nucleotides are detected. As noted above, this detection may be performed in a variety of manners, with optical detection being favored in a presently contemplated embodiment. As also described above, the detection step can include progressively scanning the sites on the array to produce image data which is processed to identify individual sites and, ultimately, the identity of the most recently attached nucleotides at each site.

At step 102, the logic determines whether the current cycle is the initial sequencing cycle. As noted above, sequencing may include a number of similar cycles of base addition, detection, and de-blocking, with from 25 to 40 or even more such cycles being presently contemplated. If the current cycle, then, is the initial cycle, an initial cycle quality control routine is performed as indicated at step 104. This routine may be configured to determine one or more qualities of the array as described in greater detail below with reference to FIG. 6. It should be noted that the initial cycle quality control routine may cause corrections to be made in the sequencing system, or may cause an alteration in the manner in which the individual sample array is handled. That is, certain steps may be re-performed, or system changes may be made based upon the initial cycle quality control as described below.

Assuming that sequencing continues following the routine 104, the logic may advance to step 106 where a routine is performed to evaluate the quality of the base addition steps of sequencing. Presently contemplated details of the base addition quality control routine 106 are described below with reference to FIG. 7. In general, however, the base addition quality control routine will evaluate parameters of the sequencing system to determine whether changes should be made to the system operating settings or whether sequencing could or should continue under the same or different conditions. As with the initial cycle quality control 104, the base addition quality control routine 106 may result in re-performing certain sequencing steps or even aborting the sequencing process altogether.

In an alternative embodiment, step 106 can be performed after step 100 and prior to step 102. This order may be advantageous if the queries and steps involved in step 106 provide information that is useful in evaluating characteristics or qualities of samples and the system at step 104. Furthermore, as set forth in further detail below in regard to FIGS. 6-8, different queries and steps exemplified for the various QC steps of FIG. 5 can be carried out in different orders than specifically exemplified herein or even repeated more than once and in a variety of combinations to suit a particular synthetic technique or synthesis system.

At step 108, the logic may call for determining whether the current cycle is the last cycle of sequencing. Several scenarios may be envisaged for this step. For example, the sequencing system may be programmed to perform only a predetermined number of cycles, with the sequencing terminating after the predetermined number of cycles have been performed. Alternatively, the quality of certain data collected by the system may be evaluated to determine whether data of a desired quality is still being collected. That is, as summarized below, in the quality control routines presently contemplated, a signal-to-noise ratio may be evaluated to determine whether the base addition operation and imaging operations can adequately distinguish the type of nucleotide that is being added at individual sites. Where such addition, or image quality, or the ability to distinguish between the nucleotides attaching at individual sites is at an undesirable level, the system may indicate that the current cycle is to be the last cycle for sequencing of a particular sample array. Other sequencing ending scenarios may, of course, be implemented. If the current cycle is determined to be the last cycle, then, end run programs may be performed as indicated at step 110. In general, such programs may include processing of image data, exporting of data, notifying a human operator or robot to remove the sample array container from the system, and so forth.

If the current cycle is not determined to be the last sequencing cycle, the logic may advance to step 112 where the blocking agents and fluorescent dyes are removed from the last nucleotide added at each site. At step 114, then, the sites or waste in the effluent stream may be detected for additional quality control. For example, the additional imaging of the sites or waste at step 114 may be used to determine whether the sites were adequately de-blocked by determining whether the dyes continue to fluoresce at each site (or at control sites, as described below). Alternatively, detection of the waste material may determine whether blocking agents that are fluorescent or that absorb radiation at a particular wavelength are present in the effluent stream at a sufficient level to indicate a desired level of de-blocking has occurred. Where such detection is not desired, step 114 is optional and may be deleted from the process. At step 116, then, a quality control routine to evaluate the de-blocking operation is performed. Details of a currently contemplated de-blocking quality control routine are described below with reference to FIG. 8. Following step 116, the logic may return to step 98 where additional bases are added for a subsequent cycle of sequencing.

The logic for carrying out and controlling a sequencing operation as presented in FIG. 5 and set forth above is merely exemplary. The logic has been exemplified in the context of particular sequencing techniques. It will be understood that the logic can be modified to accommodate different sequencing techniques. For example, pyrosequencing techniques are often carried out using nucleotides that do not have blocking groups. Accordingly, logic for carrying out pyrosequencing need not include steps related to de-blocking such as steps identified as 112, 114, and 116 in FIG. 5. As a further example, pyrosequencing techniques typically utilize secondary enzymes for detection of released pyrophosphate, such enzymes including, for example, sulfurylase and luciferase. The logic for carrying out pyrosequencing can include added steps related to adding or removing secondary enzymes. Furthermore, QC steps used in a pyrosequencing method can include steps that are related to querying the activity of the secondary enzymes and responding to information obtained from the query. Similar modification can be made to the logic for carrying out other sequencing techniques that include use of secondary reagents, such as enzymes used for detection or nucleic acid modification. For example, cycles of sequencing-by-ligation, which include a step of removing a portion of ligated probes using a restriction endonuclease or chemical cleavage of a nucleic acid strand after detection and before initiation of a new cycle, can be covered by logic that includes steps related to adding and removing the cleaving agent (such as the restriction endonuclease or chemical cleaving agent) or evaluating QC related to activity of the cleaving agent.

Throughout the sequencing process, a number of individual system parameters may be monitored and regulated in a closed-loop or open-loop manner. Again, an object of such monitoring and control is to allow for automated or semi-automated sequencing through efficient reaction and detection processes. In a presently contemplated embodiment, for example, system diagnostic parameters might include temperature of the sample or the sample container, reagent temperature, temperatures at various locations in the instrumentation, reagent volumes and flow rates, power of light sources (particularly laser light sources), pH levels downstream of the flow cell, humidity, vibration, presence of ozone, image intensities, focus quality, and so forth. Additional parameters might include reagent pump pressure, the levels of reagents remaining in reservoirs, presence of bubbles in a detection chamber (e.g., a flow cell), and computer storage space available, both for imaging data and sequence data. Moreover, in addition to these ongoing and regular checks, unusual process developments may be detected, such as the opening of a door or other access panel at a sample insertion and retrieval station (see FIG. 2), fluid overflows, and so forth. In cases where the system determines that continuing the sequencing process would not result in data being collected for each cycle, the system can make an automated decision to end the sequencing run or to flush reagents through the flow cell to preserve the sample and enter a safe state that preserves the sample until data collection can be resumed. In particular embodiments, the system can indicate an error to an operator and optionally suggest corrective measures. Alternatively or additionally, the system can make an automated diagnosis and response to the error. Thus, synthesis steps can be restarted and data collection continued either by operator intervention or by automated correction.

Transducers and circuitry for monitoring and controlling such parameters may be generally similar to those available for other process systems. For example, any form of suitable temperature transducer may be used for monitoring sample, container, reagent, and instrument temperatures. Suitable flow meters may be used for monitoring reagent volumes and flows. Conventional pressure transducers may be used for detecting reagent pump pressures, back pressures, and so forth. Logic circuits for closed-loop control or open-loop operator notification based upon detection of such parameters may include analog or digital circuits (e.g., programmed computers). In a presently contemplated embodiment, for example, the quality/process control system described above with reference to FIGS. 1 and 2 may perform these functions. As will be appreciated by those skilled in the art, the signals produced by the various transducers, where computer control is employed, will be converted to digital values which can be compared to normal operating ranges, fault limits, alarm limits, and so forth. Where possible, closed-loop control may be employed to maintain temperatures, volumes, power levels, flow rates, pressures, and so forth within acceptable ranges to permit continued sequencing. Where alarm or failure limits are reached, operation of the control routines preferably includes establishing an exception or error log and storing events in the error log so as to permit later evaluation of the performance and operation of the sequencer during particular sequencing steps, over periods of time, and so forth.

Closed-loop control of such parameters may be performed to enhance the sequencing process. For example, in a presently contemplated embodiment, the fluidics control/delivery system 18 may include heaters or coolers that can provide reagents and other fluids at desired temperatures to enhance and promote reactions with samples in the arrays. For example, heaters may be provided for elevating the temperature of the sample during certain portions of the sequencing process, and such temperatures may be regulated for the process fluids as well. Thermal transfer devices, such as heaters, coolers, heat exchangers, and so forth may be employed for this purpose. Other closed-loop control may be performed based upon the target parameters for the individual steps in the sequencing operation. Those skilled in the art will recognize, as well, that such parameters may be combined to determine when the sequencing system is operating properly, when sequencing can proceed, or when one or more such parameters is out of a normal range to the extent that sequencing should not proceed. In such cases, samples may be preserved at least for some duration of time until the sequencing system is operative within its desired parameters.

Figure 6:
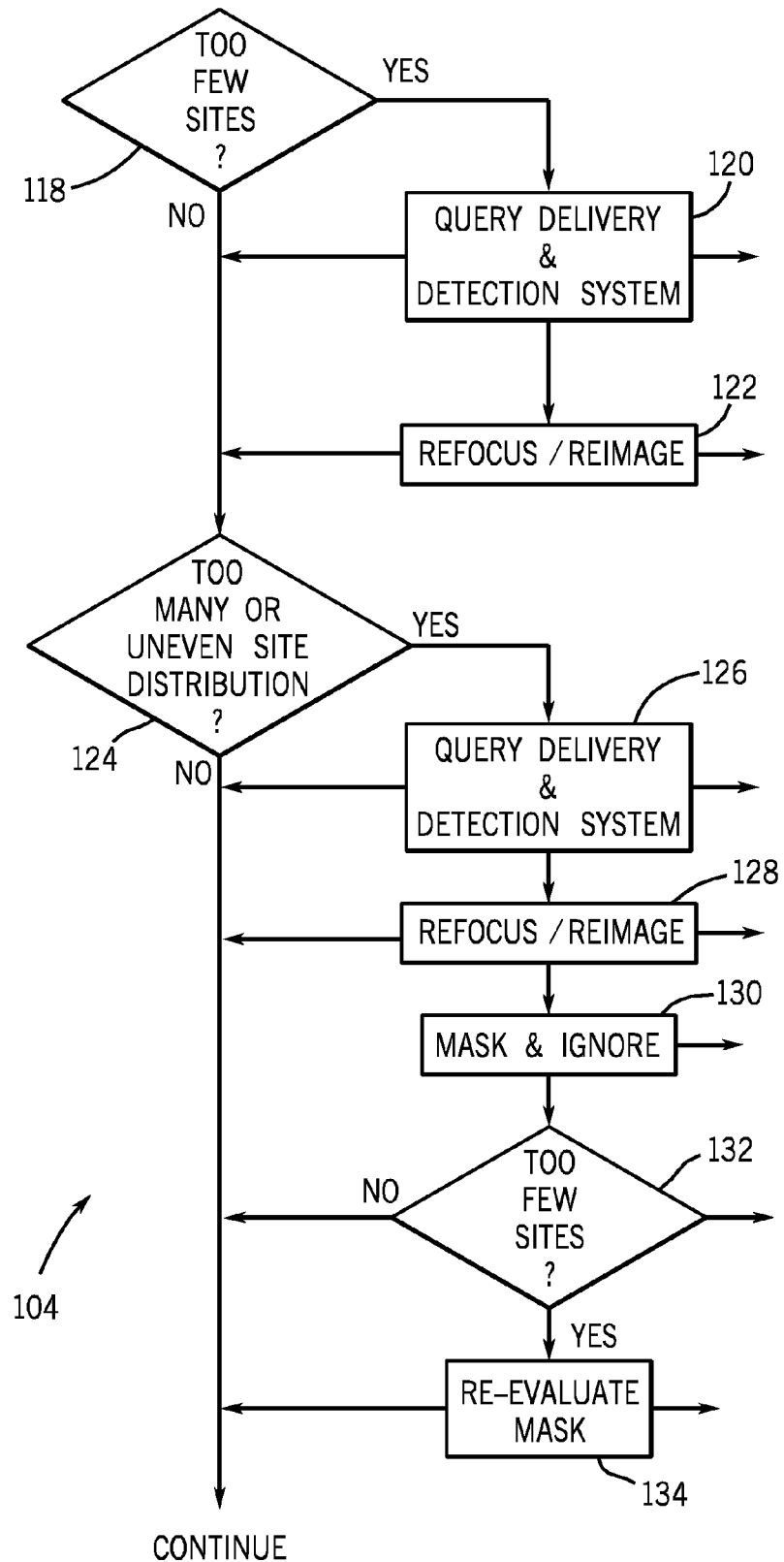
FIG. 6 is a flow chart illustrating exemplary logic for an initial sequencing cycle quality control approach in accordance with aspects of the present technique, such as to determine quality of the sample to be tested.

FIG. 6 illustrates exemplary logic that might be included in a quality control routine for an initial cycle of sequencing. The initial cycle quality control routine 104 may be designed to examine characteristics or qualities of samples and sample arrays to determine whether high-quality and sufficient sequencing data can be obtained. In a presently contemplated embodiment, for example, the routine may begin with a query as indicated at step 118 to determine whether too few sites are present and detectable in the array. This step may refer to an acceptable range or number of sites that make sequencing of the array economical in terms of the amount of data that can be collected for the amount of time and materials required to process the array. The query made at step 118 will typically be based upon the detection made at step 100 summarized with reference to FIG. 5. By way of example only, in a presently contemplated embodiment, an acceptable number of sites on which sequencing may be performed may be about 10 million sites/cm$^2$ or may be in a range between about 5 million sites/cm$^2$ and 100 million sites/cm$^2$, although developing technologies will likely increase the upper end of this range in most cases to 1000 million sites/cm$^2$ or higher. The density of sites (for example, beads) on an array can also be evaluated in terms of percent capacity such that an acceptable number of sites is indicated by a capacity between, for example, 35% and 100% (100% or full capacity being based on the ideal case where sites are evenly distributed and at a distance that is just sufficient to allow adjacent sites to be distinguished). The positions of the beads or other sites may be regularly spaced with a known separation between individual sites, or a random distribution, for example, an array of amplified clusters or a random array of beads on a surface.

If too few sites are detected or discernible from the imaging or detection operations performed in the initial cycle, control may be directed to step 120 where queries may be made of the fluid delivery or detection systems, or both systems, or other systems of the sequencer. In general, a particular density of sites or clusters will be desired. If the detected number of such sites is low or lower than desired, this may be indicated by a count of the number of sites or by determining that a number of "dark" pixels (e.g., pixels not apparently indicative of the presence of a site) is above a ceiling. Such occurrences could be due to parameters of the fluid delivery system or the detection system, or both, as well as other parameters of the sequencer. For example, absence of detected sites may be due to inadequate delivery of labeled nucleotides to the array sample or due to improper focusing of the imaging system. The query performed at step 120, then, may examine operational parameters of the type described above to determine whether proper operation is possible. Following such determinations, alterations in the system settings may be performed, and the sample may be returned for re-focusing and re-imaging, if necessary, as indicated at step 122. Similarly, the system may be returned for re-delivery of biomolecule reagents at step 98.

It should be noted that throughout the present discussion, and indeed for all of the quality control routines summarized in the present discussion, one or more of the responses may be performed, and such responses may be performed in any logical order where appropriate. For example, for the query of the delivery and detection systems, and the re-focus/re-image routine described above, these may be performed in parallel in any sequence. Moreover, for these and for other routines performed, the present discussion should not be considered as limiting. Depending upon the parameter data collected, the sequencing technique being used and the possible cause of anomalies in operation of the system or in the sequencing data obtained, other routines may be performed as well. Similarly, it may be advantageous to perform some routines before others. For example, a quick check of the operational parameters of the system, noting slight anomalies that have been corrected, may be more efficient than recycling the sample in a retrograde fashion back to an imaging station as would be called for at step 122 (assuming that the sample had been moved from the detection or imaging station). Finally, it should be noted that certain of the steps will clearly call for repeating of certain sequencing operations, altering certain sequencing operations, or even aborting sequencing of the particular sample as denoted by the arrows extending to the right in FIGS. 6, 7, and 8. It may be considered that following the various response routines described herein, a determination is made as to whether the condition that led to the action has been remedied, such that sequencing may proceed albeit by the return of the sample to a preceding operation.

In addition to determining whether too few sites are present in the sample, the initial cycle quality control routine, examining qualities of the sample, may determine whether too many sites or an uneven site distribution is present, as indicated generally at reference numeral 124. Because certain sample preparation techniques may result in an overabundance of sites, or sites that may too closely approach one another, there may be a desired limit to the number of sites in a particular sample, or to the relative density or congestion of sites in one or more regions of the array. Other indicators of sample quality that can be queried at this step include the size, shape, or morphology of sites. Typically, sites will have an expected size, shape, or morphology and deviations can be indicative of a particular problem. For example, if sites are too densely packed then a large fraction of sites will overlap each other such that overlapped sites appear as a single site having an apparent size that is larger than the size expected for a single discrete site. Similarly, sites that overlap can be identified by an apparent shape that is different than expected for a single site, such as in the case of typically circular sites that will appear as a single hourglass shape when two sites overlap. Other aberrations in size, shape, or morphology of sites can be indicative of problems in preparation of the array that occurred prior to loading the array in the system such as insufficient amplification at one or more sites or excessive amplification at one or more sites. If, upon the evaluation of the data collected at step 100 in FIG. 5, it is determined that too many sites or an undesirable site distribution is present, several approaches may be envisaged in response. At step 126, for example, the fluid delivery and detection systems may be again queried in a manner similar to that discussed with reference to step 120 above. Moreover, the imaging system may be re-focused, particularly if the detection data indicates that inadequate or unreliable image data was obtained that may have led to the determination at step 124. The re-focusing and re-imaging step 128 may be essentially similar to that performed at step 122 above, and may require return of the sample to the imaging station if it has been moved from the imaging station.

Another response to the presence of too many sites or an uneven site distribution could be the masking of certain regions or sites and ignoring image data from such regions during processing. The masking response, indicated at step 130, would generally include development of a digital mask for the pixilated images in which particular locations corresponding to particular sites are designated by a first value, and sites to be analyzed are designated by a second value. Such a binary mask would generally be stored as a lookup table that permits comparison of the location of mask pixels in subsequent sequencing cycles so that data for such locations would not be processed for analysis and sequencing. It is possible, however, that such masking could result in elimination of too many sites or even large regions of the sample array from sequencing such that pursuing further processing of the sample is not economical or is otherwise undesirable. At step 132, then, it may be desirable to determine whether the masking has resulted in too few sites. As with step 118, this inquiry may essentially consist of determining whether the number of remaining sites after digital masking make sequencing worthwhile in terms of the amount of data that can be collected. If too few sites are available for sequencing after the masking of step 130, the mask may be re-evaluated as indicated at step 134, such as to determine whether certain sites can be reliably sequenced. The mask may then be altered accordingly and sequencing may proceed. If too few sites are available for sequencing, sequencing may be interrupted altogether.

The amount of image data processed during sequencing operations tends to be massive and even quite overwhelming at times. As such, analysis of the data can prove somewhat onerous unless the data is collected, organized, and managed efficiently. Therefore, it may be advantageous to process the data such that useful data is saved and prepared for further processing while discarding data which has a high probability of not being useful. Accordingly, the use of masking, as well as other image processing utilities, may be coordinated to attain the overall goal of worthwhile sequencing data. With this in mind, it should be noted that the image data collected may be processed in various ways. For example, areas on a test sample may be selected to be imaged while other areas may be selected to be bypassed. If this type of selective imaging is done, several different options may be used to handle the data. In one embodiment, image data for only the areas flagged as areas of interest may be collected while image data for other areas may not be collected, or may be collected but not retained or not analyzed. In an alternative embodiment, image data may be collected for all areas of the sample but the data may be stored in different locations. For instance, the image data flagged as areas of interest may be stored in a first database which is used for sequencing analysis whereas the other image data may be stored in a second database. In addition, logging of image data collection may follow similar procedures, such as only logging activity for certain imaging or logging activity for all imaging but saving the logs in various locations. Also, the selective processing of image data may be based on any parameter collected during sequencing operations including, but not limited to, chemistry parameters, environmental parameters, and so forth. Therefore, in general, the image data may be handled using various selective processing schemes based on various processes including, but not limited to, the masking methods discussed above.

If any of the responses indicated at steps 126, 128, 130, or 134, or the response to the query 132 enable sequencing to proceed, then, the initial cycle quality control routine may be exited and sequencing may continue as summarized above with reference to FIG. 5.

Figure 7:
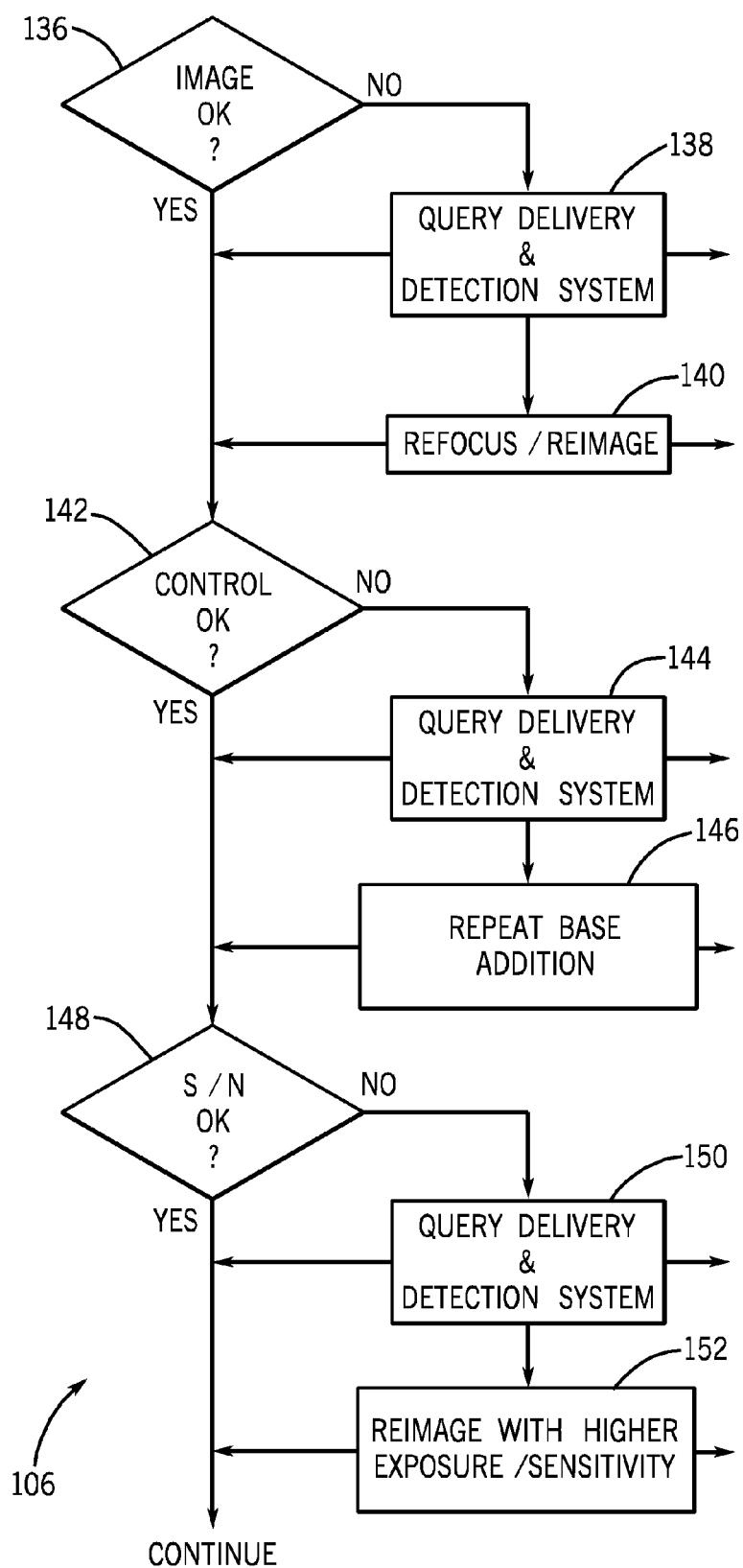
FIG. 7 is a flow chart illustrating exemplary logic for a control of quality of base or nucleotide addition in accordance with the present technique.

FIG. 7 illustrates exemplary logic for performing a base addition quality control routine 106 as described generally above with respect to FIG. 5. The routine may be performed at various stages in sequencing but will likely be performed after imaging of the array in each sequencing cycle but before image data is used to determine sequence data. The routine is essentially designed to determine whether the detection process proceeded as desired, or whether sequencer parameters should be adjusted to provide for improved imaging and detection. Because the quality of the detection performed on the sample will ultimately affect the quality of the sequencing data, it may be desirable that high-quality images be returned and it may be most useful to perform such base addition quality control routines for each and every sequencing cycle. Moreover, as discussed above, the routine may be at least one of the considerations in determining whether sequencing should continue or whether the present or even the previous sequencing cycle should be considered the last reliable cycle in which sequencing data should be retained or evaluated.

In the embodiment illustrated in FIG. 7, an initial query 136 determines whether the general image quality is acceptable. For example, while a sharp image, and particularly a consistently sharp image over the length and width of the array is desired, such factors as poor focus may result in an unacceptably blurred image. The evaluation of image quality may take a number of forms. In a presently contemplated embodiment, for example, a focus score is attributed to each image. The focus score may be based upon sharpness of the image, sharpness of particular features or marks in the image, anticipated structures visible in the image, gradients of intensities or colors detectable in the image, and so forth. Image quality can be based on an image of all or part of the array. An advantage of evaluating only a part of the array is that an image can be obtained more rapidly for purposes of determining quality prior to expending the time on obtaining a full image. If the image quality is found to be unacceptable, steps 138 and 140, or other suitable steps, may be performed in response. Steps 138 and 140 may generally correspond to steps 120 and 122 described above with reference to FIG. 6. That is, the fluid delivery and/or detection systems may be evaluated to determine whether their operating parameters are within the acceptable ranges, or the imaging system may be re-focused and the sample returned for imaging if it has been displaced from the imaging station.

Another aspect of image quality that may be monitored is the presence of bubbles within the sample. If bubbles are detected, the image data, or portions of the data, may not be adequate for further processing. For instance, the image data may appear to have blurry regions or regions where detected colors are indistinguishable. Furthermore, the presence of bubbles may signify an underlying problem with a particular sample. For instance, the bubbles may be impeding the nucleotides from attaching to the sample. The presence of bubbles may be monitored within the fluid channel via a photodiode or other detector such as one that is configured to monitor changes in the signal received at the diode responsive to the refractive index differences between air and liquid. If bubbles are detected, any number of suitable response steps may be performed. For instance, the situation may warrant returning the sample to a particular fluidics station and performing the base addition step again. In cases where the channels are filled from top-bottom with air rather than liquid, it is possible to automatically adjust the focal depth to restore the focus of the "dry" image, or simply to flow more liquid through the channel in order to remove the air bubble. Another possible response may include masking of certain regions or sites and ignoring image data for regions or sites determined to contain bubbles. Yet another response may include interrupting sequencing operations on the sample if it is determined that the bubbles are such a detriment that proper imaging is no longer possible.

It should be noted that a query similar to that of step 136, and responses such as those summarized at steps 138 and 140 may also be part of the initial cycle quality control routine summarized above with reference to FIG. 6. That is, it may be possible that the control of quality of the samples is compromised by poor functioning of the fluid delivery system or the detection system. In such cases, routines such as those intended at steps 138 and 140 may also be performed to ensure that the sample quality evaluation proceeds on the basis of reliable information. Where desired, the parameters of the sequencing system may be adjusted and the sample may be re-imaged, and the sample quality re-evaluated based upon improved input data.

As noted above, the sample arrays may be designed to facilitate certain types of quality control. For example, control clusters or sites may be included in the array that have known sequences of nucleotides. Such known sequences may, for example, be repeating sequences of the four common DNA nucleotides. Alternatively, such control sites may include homopolymer sequences of a single nucleotide type. The quality control performed in the routine 106 may rely upon expected results for such controls during successive sequencing and imaging steps carried out in parallel with sites of unknown composition for which sequence information is desired. As indicated at step 142, then, evaluation of such control sites may be made to determine whether the anticipated addition of a base has been detected. Because the sequence of such control sites is known, such evaluation may determine, for example, that no base was added, the wrong base was added, or a low yield for base coupling was detected (e.g., an anticipated characteristic dye color at a control site was weak in intensity or was obscured by another color). Another type of control that can be included is a site having a label moiety directly attached. For example, in embodiments directed to sequencing using fluorescent labels, a site can include the fluorescent labels directly attached (i.e. not via a hybridized oligonucleotide) to serve as a control for detection quality that is independent of other aspects of the sequencing chemistry (such as efficiency of hybridization and nucleotide addition).

The failure to add a base may be indicated by a single intensity in the image data that is below a desired threshold. The addition of a wrong base may be indicated by a different color signal being detected in the image data (e.g., at a control site) than was anticipated. An indicator for a low yield base coupling may, as indicated above, be a signal intensity that is lower than expected, similar to the test for no base having been added. The expected intensity can be a particular threshold level that remains unchanged for all cycles. Alternatively, the threshold level can be reduced at each cycle in accordance with an acceptable loss of yield at each step or in accordance with an empirically determined loss of yield determined from the signal detected from one or more previous cycles, as described for example in regard to signal-to-noise (S/N) ratio below.

Several responses may be envisaged for improving sequencing, image data, or sequence data where query 142 determines that the imaging of control sites was defective. For example, as indicated at step 144, the system may query the fluid delivery and detection systems to determine whether operating parameters are within acceptable ranges. Alternatively, or in addition to this step, the base addition process may be repeated as indicated at step 146. In general, step 146, as with the re-imaging steps described above, may require that the sample be returned to a fluidics station for addition of the bases.

In addition, several parameters may be used to help monitor imaging and sequencing operations. As mentioned in various passages throughout this disclosure, these may include parameters relating to chemistry (e.g., evaluating reagent delivery), parameters relating to fiducials (e.g., control clusters), sample site parameters (e.g., site quality, distribution, shape, number, and so forth), and temperature parameters (e.g., fluid temperature, array temperature, instrument temperature, and so forth). However, many other parameters may prove useful in ascertaining how successfully the sequencing operations are proceeding. For instance, various environmental parameters may be monitored to provide input as to how external factors may be affecting sequencing operations. These environmental parameters may include, without limitation, humidity, external power sources, temperature, vibration, and so forth. In addition, it may prove useful to monitor pH levels downstream of the flow cell. Doing so may yield insight as to how effectively the steps of base addition, blocking, de-blocking, and washing are progressing. It may also be desirable to monitor any phasing occurring between the individual sample sites. For instance, individual copies of a sequence at a sample site may experience cycles where nucleotides do not attach. The result is a site having heterogeneity in the length of the extended species. If at each cycle the number of truncated copies increases, then eventually the fraction of copies at the site that have been extended at every cycle is reduced. This results in the site having copies that are out of phase and a perceived reduction in S/N ratio. Eventually, this may lead to a situation where the S/N ratio degrades to such a level that sequencing data becomes unreliable. Early detection of flow cells that show high levels of sites having phasing problems can allow measures to be taken to ensure the sample is not completely lost, for example changing the sequencing reagents or checking the fluidics of the instrument. Alternatively or additionally, a decision can be made to halt reagent delivery to a sample having an undesirable number of out of phase sites. This can provide the advantage of reducing sample waste. Tracking premature phasing problems can provide the basis for a determination of the functionality of the instrument which can be responded to by alterations made by an operator or in an automated fashion according to predicted causes.

A further query that may be made in the base addition quality control routine is indicated at step 148, and may consist of determining whether the S/N ratio is within an acceptable limit. In general, as noted above, detection of colors of fluorescent dyes for individual sites may be a basis for determination of sequence data, and the ability to accurately detect such colors may be important for obtaining reliable sequence data. A poor S/N ratio may be determined, for example, by comparing intensities or colors for individual sites, or for control sites, to S/N ratios for similar sites in previous cycles. It may be anticipated that, due to a statistically acceptable decay in yield for nucleotide coupling over a series of sequencing cycles, a normal decay in S/N ratio should be anticipated. Indeed, the determination of whether sequencing should proceed through an additional cycle or even whether sequence data or image data should be analyzed or stored for a current cycle may be determined by reference to the decay in the S/N ratio or in an objective limit of this ratio. Where the S/N ratio decays abnormally or in a catastrophic manner, several responses may be in order, for example a change of reagents such as the scanning buffer on the instrument before undertaking a further cycle of sequencing chemistry and detection. It should be noted that as an alternative, or in addition to analyzing the decay in the S/N ratio, a decay in a signal from de-blocking agents in an effluent stream may be made.

Responses to a decrease in S/N ratio detected at step 148, in addition to termination of sequencing, may include querying the fluid delivery and detection systems as indicated at step 150, such as to determine whether the systems are operating within their normal parameters, or should be adjusted to permit further sequencing. Alternatively, or in addition to this, the sample may be re-imaged with a higher exposure level (e.g., higher power output for the light sources), a higher sensitivity in the detection algorithms, or a change in any other parameter that might permit the S/N ratio to be improved (step 152). For example, the time of exposure may be lengthened to allow for more photons to be collected in particular images. It may also be desirable to alter imaging parameters such as the scan rate to allow for sites to be more accurately detected, or in higher resolution. Other parameters that can be changed are the conditions for nucleotide addition. For example, as the S/N ratio reduces, each subsequent cycle can be carried out with longer incubation times or increased concentration of reagents to help better drive the nucleotide addition reaction to completion. If the S/N ratio can be improved in such manners to an acceptable level, sequencing may continue.

Figure 8:
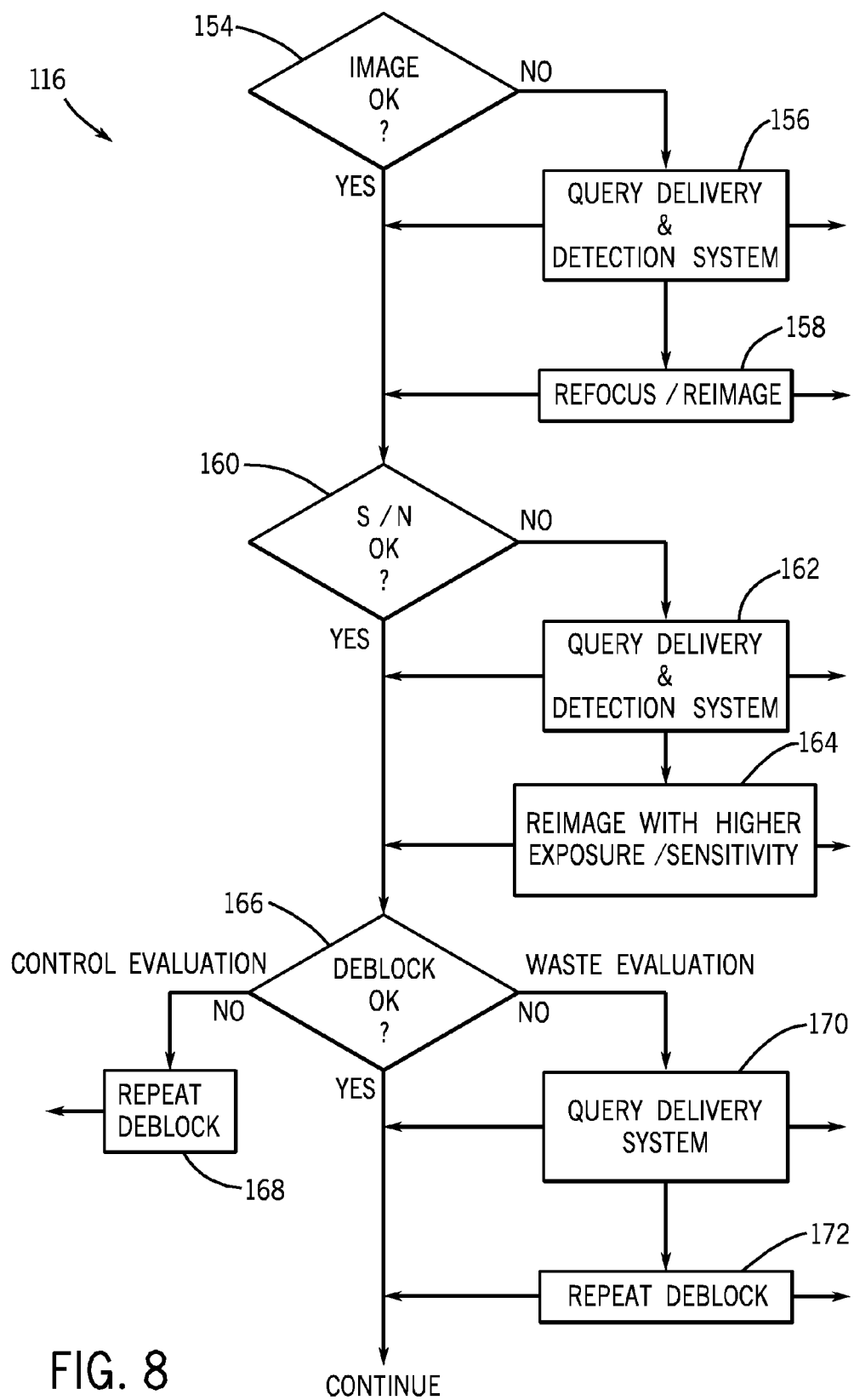
FIG. 8 is a flow chart illustrating exemplary logic for de-blocking quality control in accordance with aspects of the present technique.

FIG. 8 illustrates presently contemplated logic for a de-block quality control routine 116 as discussed generally above with reference to FIG. 5. In general, this routine is designed to determine whether dyes and de-blocking agents have been adequately removed from the last added nucleotides at the individual sites such that another nucleotide can be added in a subsequent sequencing cycle, and to ensure that the dyes of previously added nucleotides will not interfere with imaging of subsequently added nucleotides. As before, several queries may be in order to determine whether de-blocking has been adequately performed. At step 154, for example, a query may be made as to whether an image made after de-blocking is adequate for analysis. As discussed above with reference to step 136 of FIG. 7, several factors may cause insufficiently sharp or detailed images to be obtained. In a manner similar to response 138 and 140 of FIG. 7, then, the fluid delivery and detection systems may be queried, and the imaging system used to image the sample after de-blocking may be re-focused and sample may be re-imaged, as indicated at steps 156 and 158, respectively. As will be appreciated by those skilled in the art, the fluid delivery system examined at step 156, however, will be evaluated to determine whether reagents for cleaving de-blocking agents and fluorescent dyes is operating within normal limits or in a desired manner.

If the responses at steps 156 and 158 can adequately remedy the condition, a subsequent query 160 may be made. Step 160 is essentially similar to step 148 summarized above with reference to FIG. 7. That is, the system may determine whether a S/N ratio is sufficiently high to permit proper analysis of de-blocking. If the ratio is not sufficiently high or is not within an acceptable range, responses may include again querying the fluid delivery and detection systems, and re-imaging the de-blocked sample with modified imaging settings, as indicated at steps 162 and 164, respectively.

A further query in the exemplary routine 116 may include determining whether de-blocking agents have been sufficiently removed, as indicated at step 166. Two tests are presently contemplated for such evaluation, which may be performed in the alternative or both tests may be performed. In general, a first test may be based upon evaluation of control sites of the type discussed above. Such sites may be imaged to determine whether the anticipated color change (e.g., essentially the disappearance of the site from the image) has occurred. If the control sites do not indicate that effective de-blocking was performed, the de-blocking operation may be repeated as indicated at step 168. Again, repeat of the de-blocking operation may require return of the sample to a de-blocking station. If desired, sites other than control sites can also be imaged so as to query whether or not de-blocking has occurred.

Another test for de-blocking may be the evaluation of de-blocking agents in waste or an effluent stream following the de-blocking step. As will be appreciated by those skilled in the art, blocking agents may be coupled to dyes that become active and can fluoresce once the blocking agent has been removed from the nucleotides. The blocking agent can also be detectable in the effluent by absorbance at a particular wavelength. The waste stream may be tested, for example using an inline detector directed to the effluent stream, to determine whether sufficient blocking agent is detected in the waste stream. If insufficient blocking agent is detected, the possible responses may be to query the performance parameters of the fluid delivery system of the process fluids used for the de-blocking reaction and/or to repeat the de-blocking operation, as indicated at steps 170 and 172, respectively. Depending upon the sequencing chemistry used, a single moiety on the added nucleotides may serve as both blocking group for preventing extension and as a label for detecting nucleotide addition or, alternatively, added nucleotides can have separate label and blocking moieties. The methods set forth herein with regard to determining removal of a blocking group are intended to be illustrative of methods for determining removal of a label moiety and/or blocking moiety either separately or together. For example, in embodiments using separate label and blocking moieties, the moieties can be removed and detected separately or together in the effluent using methods similar to those exemplified above with regard to detecting a blocking group.

It should be noted that in all of the steps summarized in FIGS. 6, 7, and 8, logs of the operations performed and any remedial measures taken, are preferably kept. The logs may also be associated with the individual samples, and may be time-stamped to evaluate proper performance of the sequencing system. Where the sequencing operation is attended or can be attended by one or more operators, notification by visual or audible alarms may be provided to the operator indicating that attention to one or more samples or attention to one or more stations in the sequencing system may be in order.

It should also be noted that a substantial temporal decoupling of the sequencing steps and remedial measures taken in the quality control routines may exist in accordance with the present invention. That is, while sequencing systems may be established to process multiple samples and sample containers, these need not be processed through the system in any particular order, or even at the same rate. Based upon the quality of the sample, process parameters, and the outcome of the various quality control steps and routines, for example, certain samples may undergo some degree of regressive flow through the sequencing stations and sequencing steps. In certain cases, samples may be set aside or left out of the system for certain periods of time for evaluation of either the sample or the system, or both. The system control circuitry is preferably designed to track individual samples and the sequencing performed regardless of whether samples are taken out of sequence, taken in various times, or even whether samples require longer or shorter times for the various reactions, imaging, evaluation, and so forth. Such temporal decoupling may be an important feature in promoting efficient operation and high throughput of automated or semi-automated parallel sequencing of samples.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for sequencing a plurality of nucleic acids comprising:
   (a) beginning a cycle of a sequencing procedure for an array comprising a plurality of nucleic acids via a system capable of determining nucleotide sequence of the array;
   (b) evaluating a parameter of the system, wherein the parameter relates to a decay in signal-to-noise ratio over a plurality of sequencing cycles;
   (c) altering the sequencing procedure for the array based on the parameter; and
   (d) performing another cycle of the sequencing procedure for the array.

2. The method of claim 1, wherein the parameter relates to phasing between sample sites of the array.

3. The method of claim 1, wherein the parameter relates to a quality of a control cluster of the array.

4. The method of claim 1, wherein the parameter relates to a reagent used to sequence the array.

5. The method of claim 4, wherein the parameter includes a volume of the reagent.

6. The method of claim 1, wherein the parameter includes a parameter of an optical imaging system used to sequence the array.

7. The method of claim 1, wherein step (c) includes repeating introduction of nucleotides to the array.

8. The method of claim 1, wherein step (c) includes evaluating operation of a reagent delivery system.

9. The method of claim 1, wherein step (c) includes re-imaging the array.

10. The method of claim 9, wherein the array is re-imaged with a longer exposure or a greater imaging system sensitivity.

11. The method of claim 1, wherein step (c) includes selecting certain areas of the array for which imaging data will be used for sequencing.

12. The method of claim 11, wherein step (d) includes collecting imaging data for only the selected areas of the array.

13. The method of claim 11, wherein step (d) includes collecting imaging data for all areas of the array.

14. The method of claim 13, wherein the imaging data for areas of the array not selected to be used for sequencing is stored.

15. The method of claim 1, wherein step (c) includes interrupting the sequencing procedure and step (d) is not performed.

16. The method of claim 1, wherein steps (b) and (c) are performed by a human operator based on analysis generated by a computer system.

17. The method of claim 1, wherein steps (b) and (c) are performed by a computer system.

18. A method for sequencing a sample comprising a plurality of nucleic acids, comprising:
   (a) performing an automated nucleic acid sequencing operation on the sample using a laser light source;
   (b) generating data based upon the operation;
   (c) evaluating a decay in signal-to-noise ratio of the sample based upon the data;
   (d) increasing the power of the laser light source based upon the decay in signal-to-noise ratio; and
   (e) repeating steps (a) through (d).

19. A method for sequencing a plurality of nucleic acids, comprising:
   (a) performing a cycle of a sequencing procedure for an array comprising a plurality of nucleic acids via a system capable of determining nucleotide sequence of the array;
   (b) detecting a plurality of signals indicative of nucleotides present at sites of the array;
   (c) evaluating the signals to determine quality of the array; and
   (d) altering the sequencing procedure for the array based on the quality.

20. The method of claim 18, wherein the plurality of nucleic acids are located at individual sites of an array.

21. The method of claim 20, wherein step (a) further comprises adding nucleotides to sites of the array, whereby the adding is repeated in step (e).

22. The method of claim 20, wherein step (a) further comprises adding oligonucleotides to sites of the array, whereby the adding is repeated in step (e).

23. The method of claim 20, wherein the data generated in step (b) comprises image data.

24. The method of claim 23, wherein step (b) further comprises processing the image data to identify individual sites of the array.

25. The method of claim 20, wherein the automated nucleic acid sequencing operation of step (a) comprises progressively scanning the sites on the array.

26. The method of claim 20, further comprising adding a nucleotide to sites of the array prior to step (a).

27. The method of claim 18, wherein steps (a) through (d) are repeated for twenty five or more sequencing cycles.

28. The method of claim 18, wherein the automated nucleic acid sequencing operation of step (a) comprises a single imaging cycle.

29. The method of claim 19, wherein step (d) includes repeating introduction of nucleotides or oligonucleotides to the array.

30. The method of claim 19, wherein step (d) includes evaluating operation of a reagent delivery system.

31. The method of claim 19, wherein step (d) includes re-imaging the array.

32. The method of claim 31, wherein the array is re-imaged with a longer exposure or a greater imaging system sensitivity.

33. The method of claim 19, wherein step (d) includes selecting certain areas of the array for which imaging data will be used for sequencing.

34. The method of claim 33, wherein step (d) includes collecting imaging data for only the selected areas of the array.

* * * * *